United States Patent
Mellican et al.

(10) Patent No.: US 7,745,448 B2
(45) Date of Patent: Jun. 29, 2010

(54) CRYSTALLINE N-(4-(4-AMINOTHIENO[2,3-D]PYRIMIDIN-5-YL)PHENYL)-N'-(2-FLUORO-5-(TRIFLUOROMETHYL)PHENYL)UREA ETHANOLATE

(75) Inventors: Sean M. Mellican, Gurnee, IL (US); Cathie L. Linton, Waukegan, IL (US); Jianzhang Mei, Lake Forest, IL (US); Jason S. Tedrow, Santa Monica, CA (US); Nahathai Charukamnoetkanok, Pittsburgh, PA (US); Rodger Henry, Wildwood, IL (US)

(73) Assignee: Abbott Laboratories Inc., Abbott Park, IL (US)

( * ) Notice: Subject to any disclaimer, the term of this patent is extended or adjusted under 35 U.S.C. 154(b) by 650 days.

(21) Appl. No.: 11/642,395

(22) Filed: Dec. 20, 2006

(65) Prior Publication Data

US 2007/0155758 A1    Jul. 5, 2007

Related U.S. Application Data

(60) Provisional application No. 60/754,447, filed on Dec. 28, 2005.

(51) Int. Cl.
| | |
|---|---|
| *C07D 495/04* | (2006.01) |
| *A61K 31/519* | (2006.01) |
| *A61P 35/04* | (2006.01) |
| *A61P 35/02* | (2006.01) |
| *A61P 17/06* | (2006.01) |
| *A61P 9/12* | (2006.01) |

(52) U.S. Cl. .................................. 514/260.1; 544/278

(58) Field of Classification Search ................. 544/278; 514/260.1

See application file for complete search history.

(56) References Cited

U.S. PATENT DOCUMENTS 7,427,623 B2    9/2008    Adams et al.
2005/0004142 A1 *  1/2005    Adams et al. ............ 514/260.1

OTHER PUBLICATIONS

Lab. Investig. (1992), pp. 519-528, vol. 66(5), Madri, J. et. al.
Anat. Rec. (1997), 249 (1), pp. 63-73, Wilson, M. et. al.
Int. J. Cancer (1995), 63 (5) pp. 694-701, Derbyshire, E. et. al.
Arteriosclerosis, Thrombosis, and Vascular Biology (1995), 15 (11), pp. 1857-1860, Silvagno, F. et al.
J. Thorac. Cardiovasc. Surg. (2001), 122 (1), pp. 65-73, Thistlethwaite, P. et. al.
U.S. Appl. No. 11/642,397, filed Dec. 20. 2006, Sean M. Mellican.
U.S. Appl. No. 11/642,497, filed Dec. 20. 2006, Sean M. Mellican.
U.S. Appl. No. 11/642,408, filed Dec. 20. 2006, Sean M. Mellican.
U.S. Appl. No. 11/642,201, filed Dec. 20. 2006, Sean M. Mellican.
U.S. Appl. No. 11/642,399, filed Dec. 20. 2006, Sean M. Mellican.
U.S. Appl. No. 11/642,396, filed Dec. 20. 2006, Sean M. Mellican.
U.S. Appl. No. 11/642,491, filed Dec. 20, 2006, Sean M. Mellican.

* cited by examiner

*Primary Examiner*—Susanna Moore
(74) *Attorney, Agent, or Firm*—Glen J. Gesicki

(57) ABSTRACT

A crystalline N-(4-(4-aminothieno[2,3-d]pyrimidin-5-yl)phenyl)-N'-(2-fluoro-5-(trifluoromethyl)phenyl)urea ethanolate characterized in the monoclinic crystal system and $P2_1/n$ space group, when measured with radiation at 0.7107 Å, by lattice parameters a, b and c of 5.0318 Å±0.006 Å, 23.684 Å±0.002 Å and 18.877 Å±0.002 Å, respectively, and β of 90.703±0.003, ways to make it, compositions comprising it, and methods of treatment using it are disclosed.

2 Claims, No Drawings

CRYSTALLINE N-(4-(4-AMINOTHIENO[2,3-D]PYRIMIDIN-5-YL)PHENYL)-N'-(2-FLUORO-5-(TRIFLUOROMETHYL)PHENYL)UREA ETHANOLATE

This application claims priority to U.S. Provisional Application Ser. No. 60/754,447, Dec. 28, 2005.

FIELD OF THE INVENTION

This invention pertains to a crystalline N-(4-(4-aminothieno[2,3-d]pyrimidin-5-yl)phenyl)-N'-(2-fluoro-5-(trifluoromethyl)phenyl)urea ethanolate, ways to make it, compositions comprising it and methods of treatment using it.

BACKGROUND OF THE INVENTION

The compound N-(4-(4-aminothieno[2,3-d]pyrimidin-5-yl)phenyl)-N'-(2-fluoro-5-(trifluoromethyl)phenyl)urea is useful for treating diseases caused or exascerbated by upregulation or overexpression of protein tyrosine kinases.

Because the crystallinity of solvates of compounds may effect, among other physical and mechanical properties, their solubility, dissolution rate, hardness, compressability and melting point, there is an existing need in the process and therapeutic arts for identification of crystalline solvates of N-(4-(4-aminothieno[2,3-d]pyrimidin-5-yl)phenyl)-N'-(2-fluoro-5-(trifluoromethyl)phenyl)urea and ways to reproducibly make them.

SUMMARY OF THE INVENTION

One embodiment of this invention, therefore, pertains to crystalline N-(4-(4-aminothieno[2,3-d]pyrimidin-5-yl)phenyl)-N'-(2-fluoro-5-(trifluoromethyl)phenyl)urea ethanolate characterized in the monoclinic crystal system and $P2_1/n$ space group, when measured with radiation at 0.7107 Å, by lattice parameters a, b and c of 5.0318 Å±0.006 Å, 23.684 Å±0.002 Å and 18.877 Å±0.002 Å, respectively, and β of 90.703±0.003.

Another embodiment pertains to crystalline N-(4-(4-aminothieno[2,3-d]pyrimidin-5-yl)phenyl)-N'-(2-fluoro-5-(trifluoromethyl)phenyl)urea ethanolate having substantial crystalline purity and characterized in the monoclinic crystal system and $P2_1/n$ space group, when measured with radiation at 0.7107 Å, by lattice parameters a, b and c of 5.0318 Å±0.006 Å, 23.684 Å±0.002 Å and 18.877 Å±0.002 Å, respectively, and β of 90.703±0.003.

Still another embodiment pertains to a composition comprising an excipient and crystalline N-(4-(4-aminothieno[2,3-d]pyrimidin-5-yl)phenyl)-N'-(2-fluoro-5-(trifluoromethyl)phenyl)urea ethanolate characterized in the monoclinic crystal system and $P2_1/n$ space group, when measured with radiation at 0.7107 Å, by lattice parameters a, b and c of 5.0318 Å±0.006 Å, 23.684 Å±0.002 Å and 18.877 Å±0.002 Å, respectively, and β of 90.703±0.003.

Still another embodiment pertains to a method or treating a patient having a disease caused or exascerbated by upregulation or overexpression of protein tyrosine kinases comprising administering thereto a therapeutically effective amount of crystalline N-(4-(4-aminothieno[2,3-d]pyrimidin-5-yl)phenyl)-N'-(2-fluoro-5-(trifluoromethyl)phenyl)urea ethanolate characterized in the monoclinic crystal system and $P2_1/n$ space group, when measured with radiation at 0.7107 Å, by lattice parameters a, b and c of 5.0318 Å±0.006 Å, 23.684 Å±0.002 Å and 18.877 Å±0.002 Å, respectively, and β of 90.703±0.003.

Still another embodiment pertains to a process for making a crystalline N-(4-(4-aminothieno[2,3-d]pyrimidin-5-yl)phenyl)-N'-(2-fluoro-5-(trifluoromethyl)phenyl)urea ethanolate, said process comprising:

providing a mixture comprising N-(4-(4-aminothieno[2,3-d]pyrimidin-5-yl)phenyl)-N'-(2-fluoro-5-(trifluoromethyl)phenyl)urea and ethanol, wherein said N-(4-(4-aminothieno[2,3-d]pyrimidin-5-yl)phenyl)-N'-(2-fluoro-5-(trifluoromethyl)phenyl)urea is completely dissolved in said ethanol;

causing crystalline N-(4-(4-aminothieno[2,3-d]pyrimidin-5-yl)phenyl)-N'-(2-fluoro-5-(trifluoromethyl)phenyl)urea ethanolate to exist in said mixture, said N-(4-(4-aminothieno[2,3-d]pyrimidin-5-yl)phenyl)-N'-(2-fluoro-5-(trifluoromethyl)phenyl)urea ethanolate, when isolated, characterized in the monoclinic crystal system and $P2_1/n$ space group, when measured with radiation at 0.7107 Å, by lattice parameters a, b and c of 5.0318 Å±0.006 Å, 23.684 Å±0.002 Å and 18.877 Å±0.002 Å, respectively, and β of 90.703±0.003, and isolating said crystalline N-(4-(4-aminothieno[2,3-d]pyrimidin-5-yl)phenyl)-N'-(2-fluoro-5-(trifluoromethyl)phenyl)urea ethanolate.

Still another embodiment pertains to N-(4-(4-aminothieno[2,3-d]pyrimidin-5-yl)phenyl)-N'-(2-fluoro-5-(trifluoromethyl)phenyl)urea ethanolate prepared by the foregoing process.

DETAILED DESCRIPTION OF THE INVENTION

This invention pertains to discovery of a crystalline N-(4-(4-aminothieno[2,3-d]pyrimidin-5-yl)phenyl)-N'-(2-fluoro-5-(trifluoromethyl)phenyl)urea ethanolate, ways to characterize it, compositions containing it and methods of treating diseases caused or exascerbated by upregulation or overexpression of protein tyrosine kinases using it.

The term "diseases caused or exascerbated by upregulation or overexpression of protein tyrosine kinases," as used herein, means angiogenic diseases (e.g. diabetic retinopathy, retinopathy of prematurity, choroidal neovascularization due to age-related macular degeneration, infantile hemangiomas, cancer (lung, breast, stomach, bladder, colon, pancreatic, ovarian, prostate and rectal cancer and hematopoietic malignancies (leukemia and lymphoma), glioblastoma, infantile hemangioma)) (Lab. Investig. (1992), 67(4), 519-528; Anat. Rec. (1997), 249(1), 63-73; Int. J. Cancer (1995), 63(5), 694-701; Vasc. Biol. (1995), 15(11), 1857-6)), pulmonary hypertension in patients with thromboembolic disease (J. Thorac. Cardiovasc. Surg. 2001, 122 (1), 65-73) and autoimmune diseases (psoriasis, kidney rejection, graft versus host disease).

The term "amorphous," as used herein, means a supercooled liquid substance or a viscous liquid which may appear as a solid but does not have a regularly repeating arrangement of molecules maintained over a long range. Amorphous substances do not have a melting point but soften or flow above a certain temperature known as the glass transition temperature.

The term "crystalline," as used herein, means having a regularly repeating arrangement of molecules which is maintained over a long range or external face planes.

The term "crystalline N-(4-(4-aminothieno[2,3-d]pyrimidin-5-yl)phenyl)-N'-(2-fluoro-5-(trifluoromethyl)phenyl)urea ethanolate," as used herein, means a particular crystalline N-(4-(4-aminothieno[2,3-d]pyrimidin-5-yl)phenyl)-N'-(2-fluoro-5-(trifluoromethyl)phenyl)urea ethanolate, including the crystalline N-(4-(4-aminothieno[2,3-d]pyrimidin-5-yl)phenyl)-N'-(2-fluoro-5-(trifluoromethyl)phenyl) urea ethanolate of this invention.

The term "crystalline N-(4-(4-aminothieno[2,3-d]pyrimidin-5-yl)phenyl)-N'-(2-fluoro-5-(trifluoromethyl)phenyl) urea ethanolate of this invention," as used herein, means crystalline N-(4-(4-aminothieno[2,3-d]pyrimidin-5-yl)phenyl)-N'-(2-fluoro-5-(trifluoromethyl)phenyl)urea ethanolate characterized in the monoclinic crystal system and $P2_1/n$ space group, when measured with radiation at 0.7107 Å, by lattice parameters a, b and c of 5.0318 Å±0.006 Å, 23.684 Å±0.002 Å and 18.877 Å±0.002 Å, respectively and β of 90.703±0.003.

Unless stated otherwise, percentages herein are weight/weight (w/w) percentages.

The term "substantial crystalline purity," as used herein, means at least about 95% crystalline purity, preferably about 97% crystalline purity, more preferably about 99% crystalline purity, and most preferably about 100% crystalline purity.

The term "crystalline purity," as used herein, means percentage of a particular crystalline form of a compound in a sample which may contain amorphous form of the compound, one or more than one other crystalline forms of the compound other than the crystalline form of the compound of this invention, or a mixture thereof.

The term "substantial chemical purity," as used herein, means about 95% chemical purity, preferably about 97% chemical purity, more preferably about 98% chemical purity, and most preferably about 100% chemical purity.

This invention is also meant to include mixtures comprising the crystalline N-(4-(4-aminothieno[2,3-d]pyrimidin-5-yl)phenyl)-N'-(2-fluoro-5-(trifluoromethyl)phenyl)urea ethanolate of this invention in combination with one or more than one other crystalline forms of N-(4-(4-aminothieno[2,3-d]pyrimidin-5-yl)phenyl)-N'-(2-fluoro-5-(trifluoromethyl)phenyl)urea ethanolate.

It is meant to be understood that each component of mixtures consisting essentially of two or more crystalline forms of N-(4-(4-aminothieno[2,3-d]pyrimidin-5-yl)phenyl)-N'-(2-fluoro-5-(trifluoromethyl)phenyl)urea ethanolate may have varying degrees of chemical purity and that, in a preferred embodiment for the practice of this invention, in mixtures comprising different forms of N-(4-(4-aminothieno[2,3-d]pyrimidin-5-yl)phenyl)-N'-(2-fluoro-5-(trifluoromethyl)phenyl)urea ethanolate, each component is substantially chemically pure.

The term "solvent," as used herein, means a liquid substance in which a compound is soluble or partially soluble enough at a given concentration to dissolve or partially dissolve the compound.

The term "anti-solvent," as used herein, means a liquid in which a compound is insoluble enough at a given concentration to be effective for precipitating that compound.

Solvents and anti-solvents may be mixed with or without emulsification.

It is meant to be understood that, because many solvents and anti-solvents contain impurities, the level of impurities in solvents and anti-solvents for the practice of this invention, if present, are at a low enough concentration that they do not interfere with the intended use of the solvent in which they are present.

Causing a crystalline N-(4-(4-aminothieno[2,3-d]pyrimidin-5-yl)phenyl)-N'-(2-fluoro-5-(trifluoromethyl)phenyl) urea ethanolate to exist in a mixture in which it has completely dissolved is known as nucleation.

For the practice of this invention, nucleation may be made to occur by means such as solvent removal, temperature change, solvent-miscible anti-solvent addition, solvent-immiscible anti-solvent addition, seed crystal addition of a crystalline N-(4-(4-aminothieno[2,3-d]pyrimidin-5-yl)phenyl)-N'-(2-fluoro-5-(trifluoromethyl)phenyl)urea ethanolate, chafing or scratching the interior of the container, preferably a glass container, in which nucleation is meant to occur with an implement such as a glass rod or a glass bead or beads, or a combination of the foregoing.

For the practice of this invention, nucleation may be followed by crystal growth, accompanied by crystal growth, or followed and accompanied by crystal growth during which, and as a result of which, the percentage of N-(4-(4-aminothieno[2,3-d]pyrimidin-5-yl)phenyl)-N'-(2-fluoro-5-(trifluoromethyl)phenyl)urea ethanolate increases.

It is meant to be understood that airborne seed crystals of a crystalline N-(4-(4-aminothieno[2,3-d]pyrimidin-5-yl)phenyl)-N'-(2-fluoro-5-(trifluoromethyl)phenyl)urea ethanolate may also cause nucleation in a mixture comprising N-(4-(4-aminothieno[2,3-d]pyrimidin-5-yl)phenyl)-N'-(2-fluoro-5-(trifluoromethyl)phenyl)urea ethanolate and solvent wherein the N-(4-(4-aminothieno[2,3-d]pyrimidin-5-yl)phenyl)-N'-(2-fluoro-5-(trifluoromethyl)phenyl)urea ethanolate has completely dissolved.

The term "seed crystal," as used herein, means a particular crystalline form of a substance having mass. It is meant to be understood that such a crystal may be small enough to be airborne or invisible to the eye without means of detection.

The term "isolating" as used herein, means separating a crystalline N-(4-(4-aminothieno[2,3-d]pyrimidin-5-yl)phenyl)-N'-(2-fluoro-5-(trifluoromethyl)phenyl)urea ethanolate and solvent, anti-solvent, or a mixture comprising solvent and anti-solvent. This is typically accomplished by means such as centrifugation, filtration with or without vacuum, filtration with positive pressure, distillation, evaporation or a combination thereof.

A therapeutically acceptable amount of a crystalline N-(4-(4-aminothieno[2,3-d]pyrimidin-5-yl)phenyl)-N'-(2-fluoro-5-(trifluoromethyl)phenyl)urea ethanolate depends on recipient of treatment, disorder being treated and severity thereof, composition containing it, time of administration, route of administration, duration of treatment, its potency, its rate of clearance and whether or not another drug is co-administered. The amount of a crystalline N-(4-(4-aminothieno[2,3-d]pyrimidin-5-yl)phenyl)-N'-(2-fluoro-5-(trifluoromethyl)phenyl)urea ethanolate used to make a composition to be administered daily to a patient in a single dose or in divided doses is from about 0.03 to about 200 mg/kg body weight. Single dose compositions contain these amounts or a combination of submultiples thereof.

A crystalline N-(4-(4-aminothieno[2,3-d]pyrimidin-5-yl)phenyl)-N'-(2-fluoro-5-(trifluoromethyl)phenyl)urea ethanolate may be administered with or without an excipient. Excipients include but are not limited to, for example, encapsulating materials and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising and made with a crystalline N-(4-(4-aminothieno[2,3-d]pyrimidin-5-yl)phenyl)-N'-(2-fluoro-5-(trifluoromethyl)phenyl) urea ethanolate to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising and made with a crystalline N-(4-(4-aminothieno[2,3-d]pyrimidin-5-yl)phenyl)-N'-(2-fluoro-5-(trifluoromethyl)phenyl)urea ethanolate to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising and made with a crystalline N-(4-(4-aminothieno[2,3-d]pyrimidin-5-yl)phenyl)-N'-(2-fluoro-5-(trifluoromethyl)phenyl)urea ethanolate to be administered osmotically include, for example, chlorofluorohydrocarbons, ethanol, water, mixtures thereof and the like. Excipients for preparation of compositions comprising and made with a a crystalline N-(4-(4-aminothieno[2,3-d]pyrimidin-5-yl)phenyl)-N'-(2-fluoro-5-(trifluoromethyl)phenyl)urea ethanolate to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising and made with a crystalline N-(4-(4-aminothieno[2,3-d]pyrimidin-5-yl)phenyl)-N'-(2-fluoro-5-(trifluoromethyl)phenyl)urea ethanolate to be administered rectally or vaginally include, but are not limited to, cocoa butter, polyethylene glycol, wax, mixtures thereof and the like.

The following examples are presented to provide what is believed to be the most useful and readily understood description of procedures and conceptual aspects of this invention.

EXAMPLE 1

A mixture of 1-(4-nitrophenyl)ethanone (15 g), malononitrile (6 g), ammonium acetate (7 g) and acetic acid (10 mL) in benzene (200 mL) at reflux was stirred for 18 hours with azeotropic removal of water, cooled, poured into water, and extracted with ethyl acetate. The combined extracts were washed with water and brine and dried ($MgSO_4$), filtered and concentrated. The concentrate was flash chromatographed on silica gel with 25% ethyl acetate/hexanes.

EXAMPLE 2

EXAMPLE 58A (4.14 g) in ethanol (200 mL) and THF (80 mL) at 25° C. was treated sequentially with sulfur (621 mg) and triethylamine (1.82 mg), stirred for 18 hours and filtered. The filtrant was absorbed onto silica and flash column chromatographed with 3:2 hexanes/ethyl acetate.

EXAMPLE 3

EXAMPLE 2 (1.23 g) in formamide (20 mL) between 150° C. and 160° C. was stirred for 19 hours, cooled, and filtered.

EXAMPLE 4

EXAMPLE 3 (500 mg) in THF (30 mL), water (15 mL), and ethanol (40 mL) at 50° C. was treated with iron powder (0.616 g), heated between 70° C. and 80° C. for two hours and filtered through diatomaceous earth (Celite®) while hot. The filtrant was washed with THF (10 mL) and ethanol and the combined filtrates were concentrated. The rconcentrate was partitioned between water and ethyl acetate and the aqueous phase was extracted three times with ethyl acetate. The combined extracts were washed with brine and dried ($MgSO_4$), filtered and concentrated.

EXAMPLE 5

EXAMPLE 4 (40 mg) in dichloromethane (3 mL) at 0° C. was treated with 1-fluoro-2-isocyanato-4-(trifluoromethyl)benzene (24 μL), stirred for 18 hours while gradually warming to 25° C. and filtered. The filtrant was dried under vacuum. $^1H$ NMR (300 MHz, DMSO-$d_6$) δ 9.40 (s, 1H); 8.98 (d, 1H); 8.63 (dd, 2.1 Hz, 1H); 8.35 (s, 1H); 7.63 (d, 2H); 7.55-7.39 (m, 5H).

EXAMPLE 6

EXAMPLE 5 in ethanol at 70° C. was cooled and filtered.

Single crystal data were obtained using an XDS-2000/X-ray diffractometer equipped with a 2 kW normal focus X-ray tube and a Peltier cooled germanium solid-state detector (Scintag Inc., Sunnyvale, Calif.). The data were processed using DMSNT software (version 1.37). The X-ray source was a molybdenum filament (Mo—Kα at 0.7107 Å) operated at 45 kV and 40 mA.

The foregoing is meant to be illustrative of the invention and not intended to limit it to the disclosed embodiments. Variations and changes obvious to one skilled in the art are intended to be within the scope and nature of the invention as defined in the claims.

We claim:

1. Crystalline N-(4-(4-aminothieno[2,3-d]pyrimidin-5-yl)phenyl)-N'-(2-fluoro-5-(trifluoromethyl)phenyl)urea ethanolate characterized in the monoclinic crystal system and $P2_1/n$ space group, when measured with radiation at 0.7107 Å, by lattice parameters a, b and c of 5.0318 Å±0.006Å, 23.684 Å±0.002 Å and 18.877 Å±0.002 Å, respectively, and β of 90.703±0.003.

2. Crystalline N-(4-(4-aminothieno[2,3-d]pyrimidin-5-yl)phenyl)-N'-(2-fluoro-5-(trifluoromethyl)phenyl)urea ethanolate having substantial crystalline purity and characterized in the monoclinic crystal system and $P2_1/n$ space group, when measured with radiation at 0.7107 Å, by lattice parameters a, b and c of 5.0318 Å±0.006 Å, 23.684 Å±0.002 Å and 18.877 Å±0.002 Å, respectively, and β of 90.703±0.003.

* * * * *